US010024790B2

(12) United States Patent
Ahner et al.

(10) Patent No.: US 10,024,790 B2
(45) Date of Patent: Jul. 17, 2018

(54) IMAGING A TRANSPARENT ARTICLE

(71) Applicant: Seagate Technology LLC, Cupertino, CA (US)

(72) Inventors: Joachim Walter Ahner, Livermore, CA (US); David M. Tung, Livermore, CA (US); Samuel Kah Hean Wong, Johor Bahru (MY); Henry Luis Lott, Fremont, CA (US); Stephen Keith McLaurin, Sunnyvale, CA (US); Maissarath Nassirou, Fremont, CA (US); Florin Zavaliche, San Ramon, CA (US)

(73) Assignee: Seagate Technology LLC, Cupertino, CA (US)

( * ) Notice: Subject to any disclaimer, the term of this patent is extended or adjusted under 35 U.S.C. 154(b) by 361 days.

(21) Appl. No.: 14/046,596

(22) Filed: Oct. 4, 2013

(65) Prior Publication Data

US 2014/0098370 A1   Apr. 10, 2014

Related U.S. Application Data

(60) Provisional application No. 61/710,436, filed on Oct. 5, 2012.

(51) Int. Cl.
*G01N 21/55* (2014.01)
*G01N 21/47* (2006.01)
*G01N 21/95* (2006.01)

(52) U.S. Cl.
CPC ......... *G01N 21/55* (2013.01); *G01N 21/4738* (2013.01); *G01N 21/95* (2013.01)

(58) Field of Classification Search
CPC .... G01N 21/9506; G01N 21/55; G01N 21/47; G01N 21/4738; G01N 21/94; G01N 21/896; G01N 21/958; G01M 11/0278
See application file for complete search history.

(56) References Cited

U.S. PATENT DOCUMENTS

| | | | | |
|---|---|---|---|---|
| 3,988,068 A | * | 10/1976 | Sprague | G01M 11/0278 356/124 |
| 5,355,213 A | * | 10/1994 | Dotan | G01N 21/8806 356/124 |
| 5,627,638 A | * | 5/1997 | Vokhmin | 356/124 |
| 5,790,247 A | * | 8/1998 | Henley et al. | 356/237.1 |
| 5,973,839 A | | 10/1999 | Dorsel | |
| 6,226,080 B1 | | 5/2001 | Takeuchi et al. | |
| 7,511,807 B2 | | 3/2009 | Fang et al. | |
| 2004/0207836 A1 | * | 10/2004 | Chhibber | G01N 21/4738 356/237.4 |
| 2005/0141843 A1 | * | 6/2005 | Warden et al. | 385/141 |

(Continued)

FOREIGN PATENT DOCUMENTS

| | | |
|---|---|---|
| JP | 2012-185121 | 9/2012 |
| WO | 96-05503 | 2/1996 |

OTHER PUBLICATIONS

Ahner, Joachim Walter et al., "Imaging a transparent Article", International Search Report and Written Opinion, dated Jan. 16, 2014, 13 pages.

*Primary Examiner* — Dominic J Bologna

(57) ABSTRACT

Provided herein is an apparatus, comprising a first photon emitter configured to emit photons into an article from a circumferential edge of the article, and a photon detector array configured to detect photons scattered from features of the article.

19 Claims, 11 Drawing Sheets

(56) References Cited

U.S. PATENT DOCUMENTS

2006/0092276 A1    5/2006   Ariglio et al.
2006/0192952 A1    8/2006   Gahagan et al.
2011/0066382 A1    3/2011   Adams
2012/0044346 A1*   2/2012   Chou ................. G01N 21/9505
                                                                                348/131

* cited by examiner

IMAGING A TRANSPARENT ARTICLE

RELATED APPLICATIONS

This application claims the benefit of U.S. Provisional Patent Application No. 61/710,436, filed Oct. 5, 2012, by Ahner et al.

BACKGROUND

An article fabricated on a production line may be inspected for certain features, including defects that might degrade the performance of the article or a system including the article. For instance, a glass substrate for a hard disk may be inspected for certain surface features, including surface and subsurface defects that might hinder follow on production steps (e.g., washing, sputtering, polishing, and/or etching) and further degrade the performance of the disk or the hard disk drive.

In some instances, an imaging apparatus includes a camera to record images of features of a transparent article to use in performing detection, identification, and/or shape analysis of the features. For image based feature detection, the transparent article is illuminated by a light source positioned above the article while a camera records images. In such an arrangement, a majority of the light projected on the transparent article penetrates and refracts through the article while a small fraction of the light is reflected back to the camera due to the transparency of the article. Consequently, some defects may go undetected.

SUMMARY

Provided herein is an apparatus, comprising a first photon emitter configured to emit photons into an article from a circumferential edge of the article, and a photon detector array configured to detect photons scattered from features of the article.

These and other features and aspects of the concepts described herein may be better understood with reference to the following drawings, description, and appended claims.

DRAWINGS

FIGS. 1A-1E provide a schematic illustrating detection of surface features of articles in accordance with some embodiments.

Figure 4:
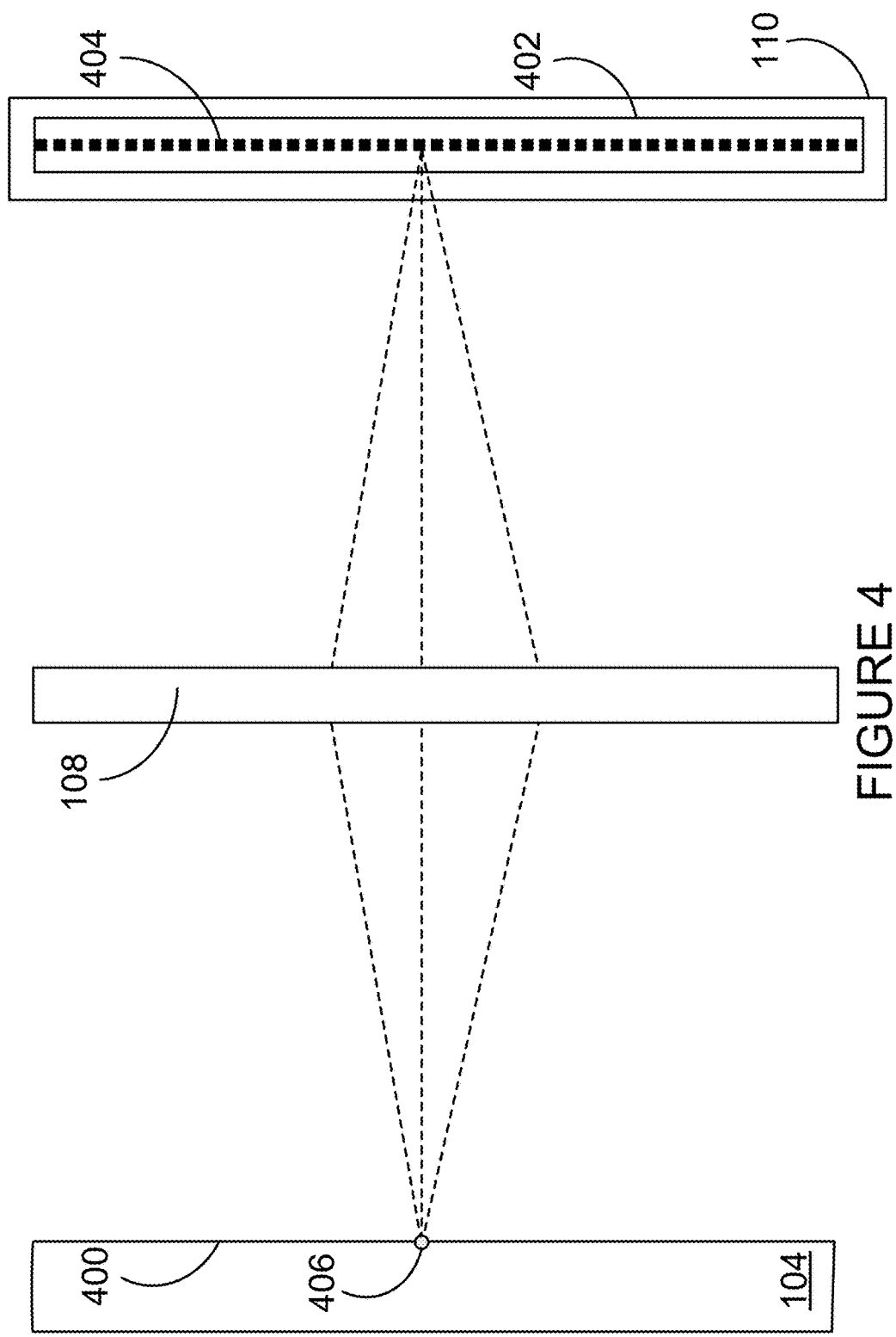

FIG. 4 provides a schematic illustrating photons scattering from a surface feature of an article, through an optical component, and onto a photon detector array in accordance with an embodiment.

Figure 5:
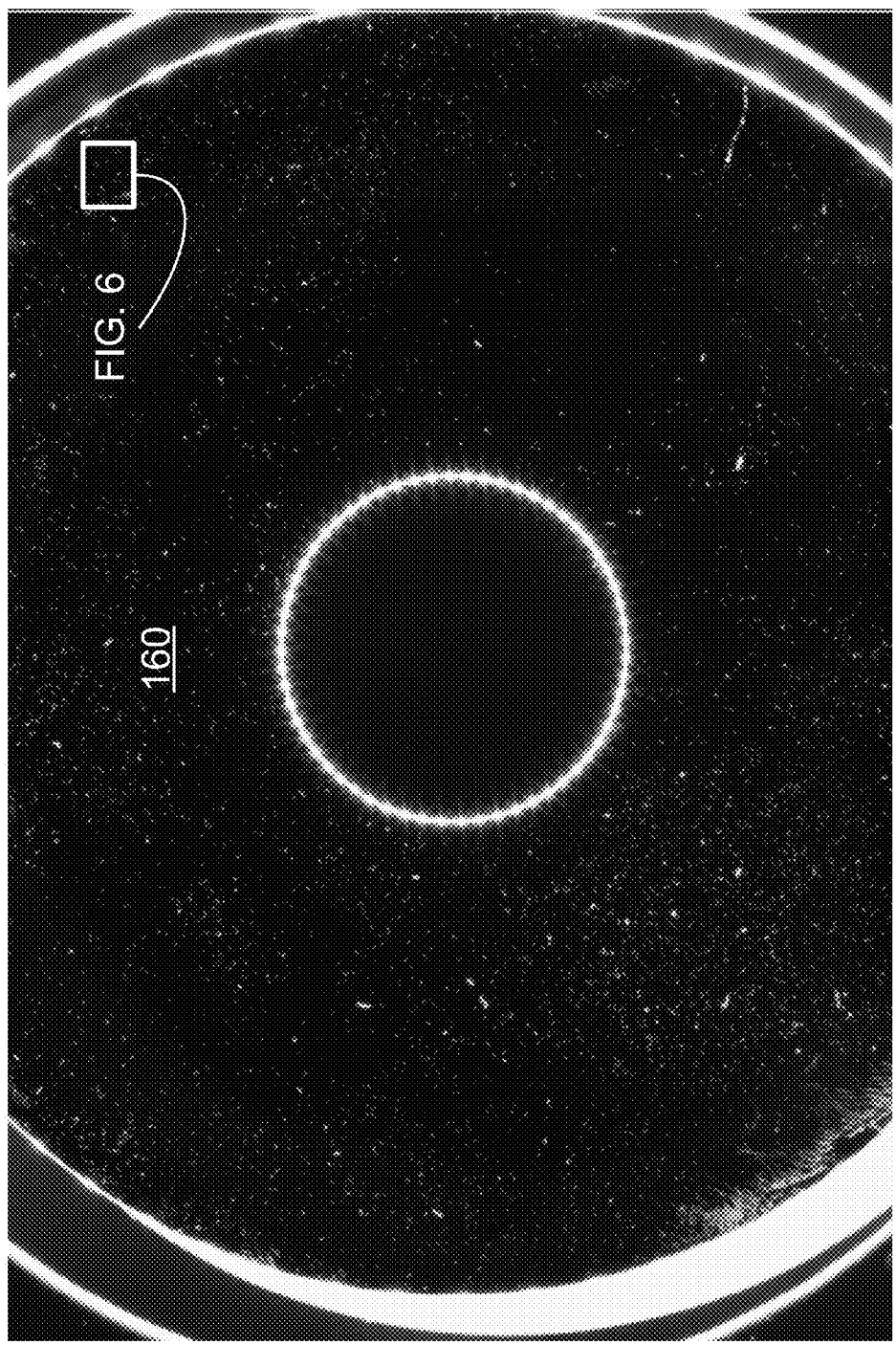

FIG. 5 provides an illustrative example of an image of a surface features map of an article in accordance with an embodiment.

Figure 6:
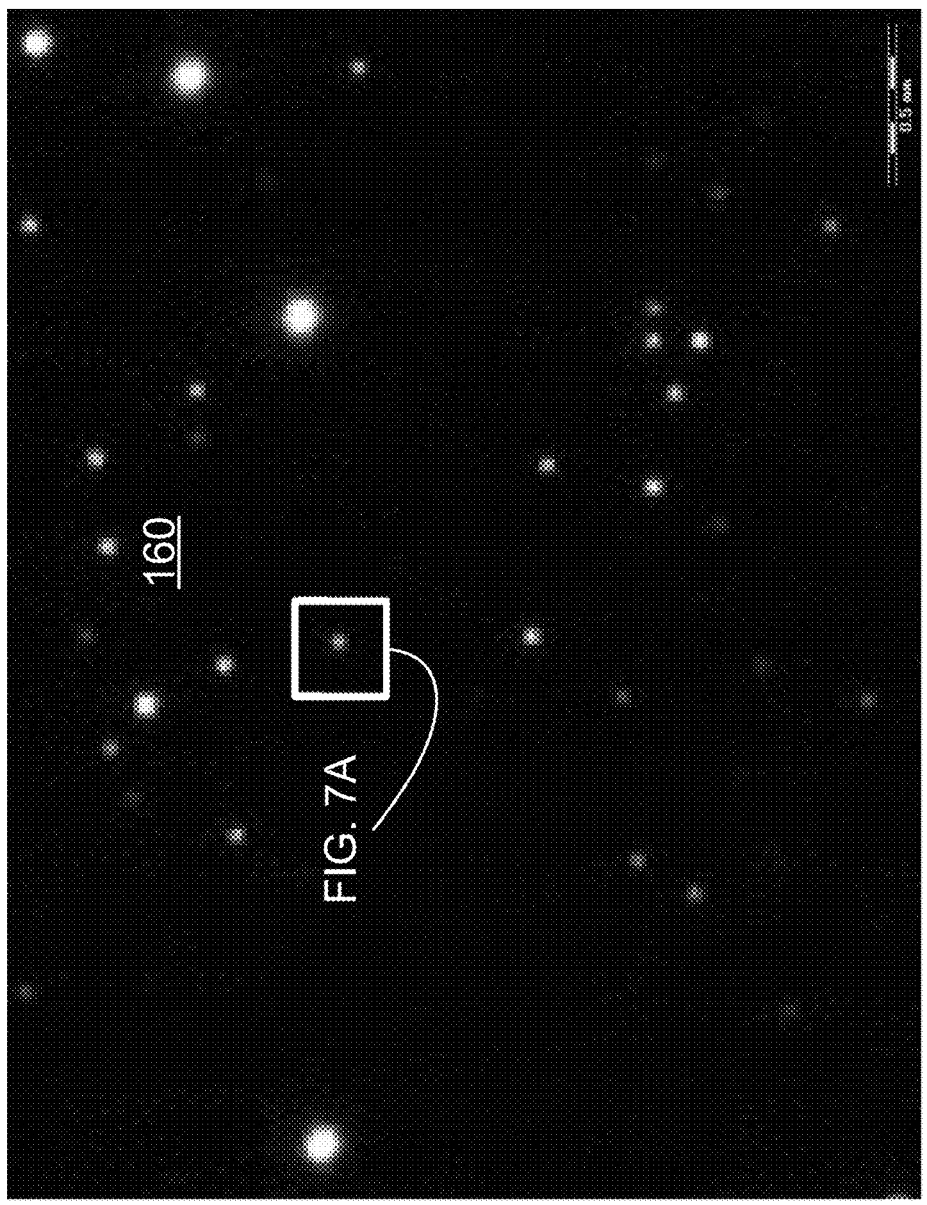

FIG. 6 provides an illustrative example of a close-up image of the surface features map provided in FIG. 5.

Figure 7A:
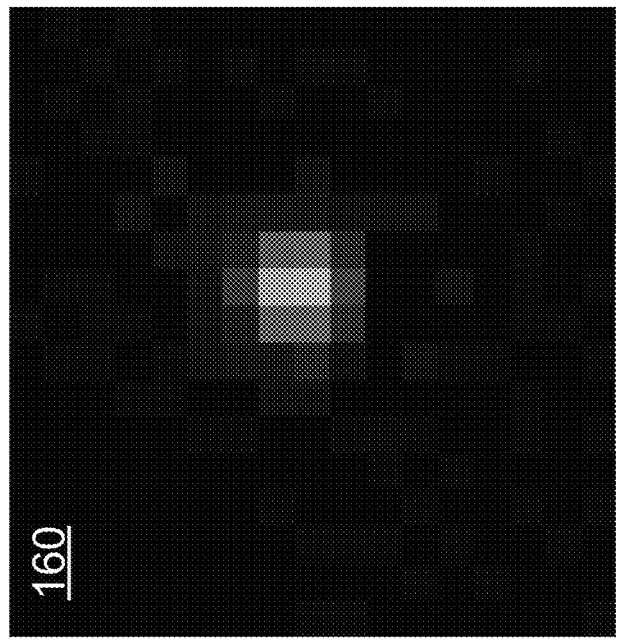

FIG. 7A (top) provides an illustrative example of a close-up image of the surface feature from the surface features map provided in FIG. 6, and FIG. 7A (bottom) provides a photon scattering intensity distribution of the surface feature.

Figure 7B:
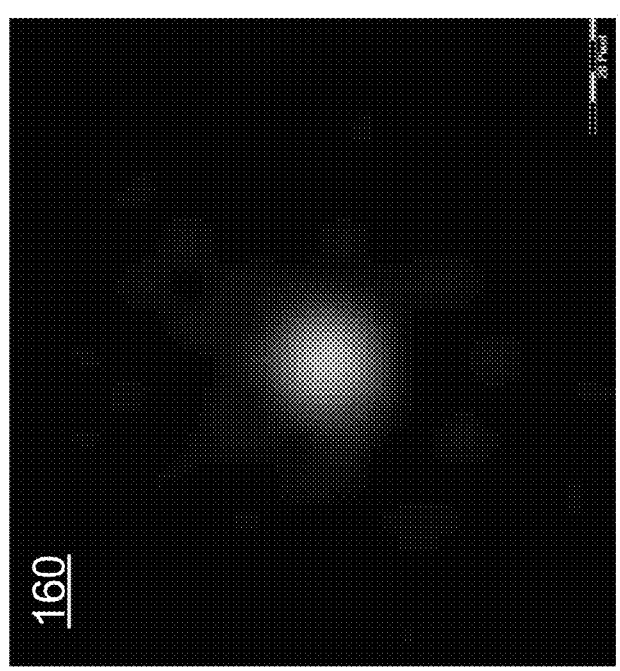

FIG. 7B (top) provides an illustrative example of a pixel-interpolated image of the surface feature from FIG. 7A, and FIG. 7B (bottom) provides an illustrative example of a pixel-interpolated photon scattering intensity distribution of the surface feature.

DESCRIPTION

Before various embodiments are described in greater detail, it should be understood by persons having ordinary skill in the art that the embodiments are not limiting, as elements in such embodiments may vary. It should likewise be understood that a particular embodiment described and/or illustrated herein has elements which may be readily separated from the particular embodiment and optionally combined with any of several other embodiments or substituted for elements in any of several other embodiments described herein.

It should also be understood by persons having ordinary skill in the art that the terminology used herein is for the purpose of describing the certain concepts, and the terminology is not intended to be limiting. Unless indicated otherwise, ordinal numbers (e.g., first, second, third, etc.) are used to distinguish or identify different elements or steps in a group of elements or steps, and do not supply a serial or numerical limitation on the elements or steps of the embodiments thereof. For example, "first," "second," and "third" elements or steps need not necessarily appear in that order, and the embodiments thereof need not necessarily be limited to three elements or steps. It should also be understood that, unless indicated otherwise, any labels such as "left," "right," "front," "back," "top," "bottom," "forward," "reverse," "clockwise," "counter clockwise," "up," "down," or other similar terms such as "upper," "lower," "aft," "fore," "vertical," "horizontal," "proximal," "distal," and the like are used for convenience and are not intended to imply, for example, any particular fixed location, orientation, or direction. Instead, such labels are used to reflect, for example, relative location, orientation, or directions. It should also be understood that the singular forms of "a," "an," and "the" include plural references unless the context clearly dictates otherwise.

Unless defined otherwise, all technical and scientific terms used herein have the same meaning as commonly understood by persons of ordinary skill in the art to which the embodiments pertain.

An article fabricated on a production line may be inspected for certain features, including defects, such as particle and stain contamination, scratches and voids, that might degrade the performance of the article or a system including the article. For example, a transparent article, such as a glass substrate, may be inspected for certain surface features, including surface and/or subsurface features, such as particle and stain contamination, pits, bumps, scratches and/or voids. It is appreciated that without inspecting a transparent article for surface features, a finished surface of an article, such as a hard disk for a hard disk drive, may be contaminated. Further, the contamination of the finished surface of an article may lead to scratch formation, debris generation, and/or corruption of the spacing between the hard disk and a read-write head. As such, the apparatus and methods described herein provide a mechanism to correct manufacturing trends leading to surface and/or subsurface defects to increase product quality.

Provided herein are apparatus and methods for inspecting transparent articles to detect and/or map certain features (e.g., surface and/or subsurface defects). In some embodiments described herein, an apparatus includes a photon emitter that directs photons into an internal region of a transparent article, such as a glass substrate for a hard disk, to illuminate the article by causing internal reflection of the photons therein. In some instances, the photon emitter is configured to direct photons into the internal region from an outer circumferential edge and/or an inner circumferential edge that results in an angle of incidence that is greater than or equal to the critical angle of the article. In this way, a majority or a total internal reflection ("TIR") of the photons may be achieved. If the article includes surface features, the photons will scatter at the location of the surface features, which may be detected by a photon detector array and further imaged for imaged-based feature detection and inspection. As such, the methods and apparatus described herein, allow for greater visibility and detectability of surface features of a transparent article.

Figure 1A:
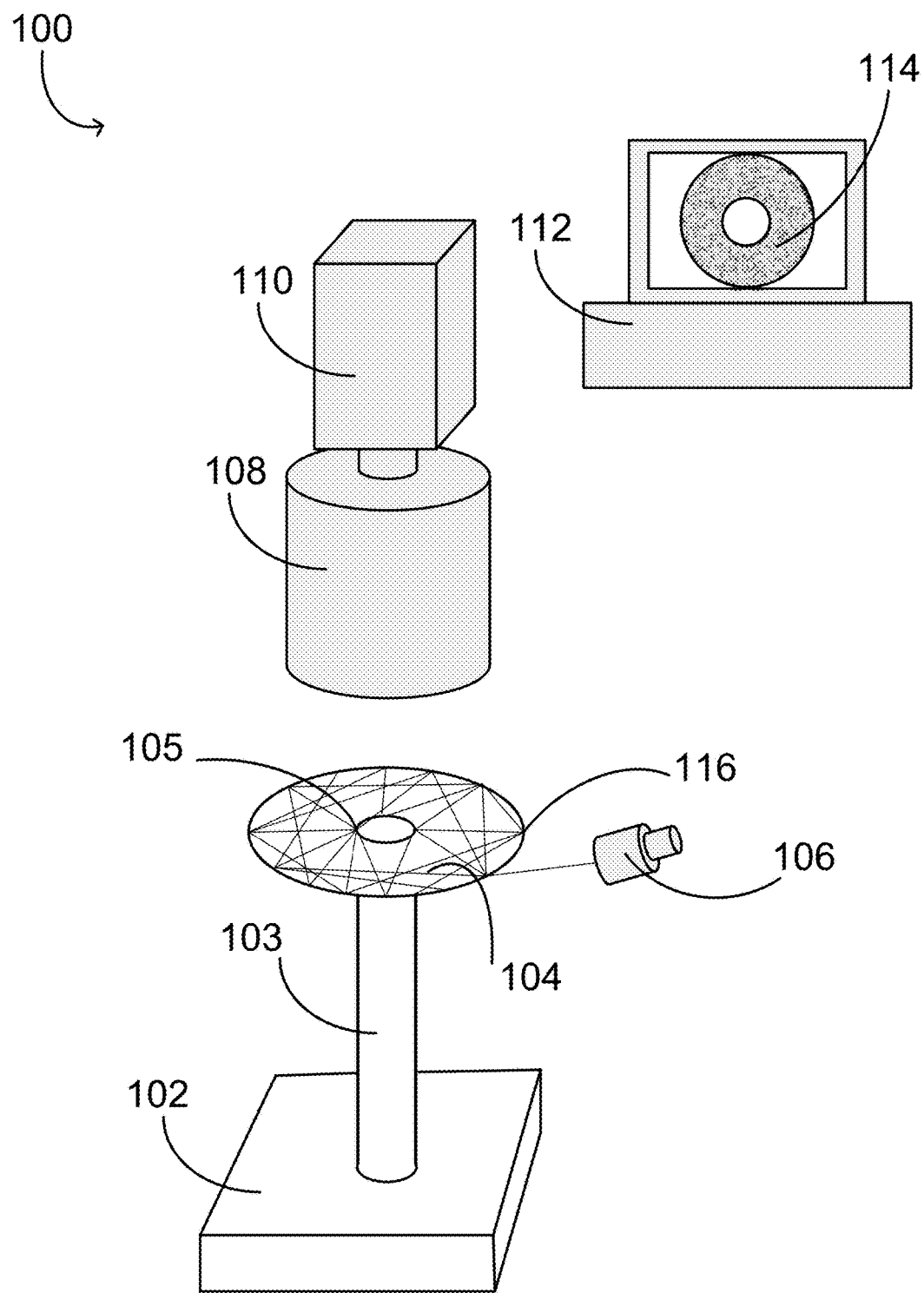

Referring to FIG. 1A, a schematic illustrating detection of surface features of articles is provided in accordance with an embodiment. The apparatus 100 includes, but is not limited to, a stage 102 and a cylindrical stage 103 configured to hold an article 104, a photon emitter 106, an optical set up 108, a camera 110 and a computer 112 displaying a surface features map 114 of a surface of the article 104 in accordance with an embodiment. It is appreciated that the apparatus and methods described herein are illustrations of certain embodiments and are not intended to limit the scope of the concepts described herein.

In some embodiments, detection and inspection of features of article 104, such as a transparent article, may be performed by directing photons from photon emitter 106 into an internal region of article 104 to internally reflect photons therein. When photons scatter from a location of a feature of article 104, the optical set up 108 and/or photon detector array (not shown) detects the scattered photons. The article 104 is imaged by camera 110, surface features of the article 104 are mapped, and used to analyze the surface features of article 104.

Before proceeding to further describe the various components of apparatus 100, it is appreciated that article 104 as described herein may be, but is not limited to, workpieces of magnetic recording media (e.g., hard disks for hard disk drives), semiconductor wafers, a workpieces having one or more optically smooth surfaces, and/or a workpieces in any stage of manufacture. In some embodiments, the article 104 may be a transparent article, such as a glass substrate for a hard disk. In some instances, the article 104 may be a glass substrate with a metallic finish, a quartz-based article, a clear oxide article, and/or a silica-based article. In some embodiments, article 104 may be an optical lens, an optical device, a diamond, and/or a transparent article that may be used for image-based feature inspection and analysis.

Referring now to stage 102, in some embodiments, the stage 102 may be a piezoelectric-controlled stage, such as atomic force microscopy ("AFM") stage. Stage 102 supports cylindrical stage 103, which further supports and holds article 104 for imaging. In some embodiments, the stage 102 may be adjusted to ensure article 104 is properly imaged. For instance, stage 102 may be configured to adjust article 104 at an angle relative to photon emitter 106 to ensure that photons directed from photon emitter 106 are internally reflected within an internal region of the article 104. For example, the stage 102 may translate article 104 in an x, y, and/or z directions in accordance with the Cartesian coordinate system to adjust the angle of article 104 with respect to photon emitter 106. In some instances, stage 102 may be configured to hold the article 104 and the cylindrical stage 103 stationary while the article 104 is being illuminated. For example, as illustrated in FIG. 1, the stage 102 holds the article 104 stationary to allow the entire article to be illuminated in a single instance, instead of scanning and/or rotating the article to illuminate the article in a piecemeal fashion. By holding the article 104 stationary and illuminating the entire article in a single instance, it is appreciated that certain efficiencies in time and productivity are gained. For example, the time to image an article is reduced from hours to minutes (or less), and furthermore, a greater volume of articles may be imaged for inspection and feature analysis in a single hour (e.g., a disk may be inspected and imaged within one second, resulting in the inspection and imaging of 3600 disks in an hour). Although certain efficiencies are provided by holding article 104 stationary while the article 104 is illuminated, it is appreciated that in certain instances stage 102 may be configured to rotate to illuminate a region of interest of article 104.

Referring now to cylindrical stage 103, the cylindrical stage 103 is supported by stage 102 at one end and supports article 104 at the other end. The cylindrical stage 103 includes a fastener and/or clamping system (not shown) secured to an inner circumferential edge 105 of the article. The cylindrical stage 103 supports and holds article 104 in a manner that allows a substantially homogeneous medium with a lower index of refraction than the index of refraction of article 104 to surround the surfaces (e.g., upper surface, lower surface, inner and/or outer circumferential edges) of article 104 to facilitate internal reflection of photons within article 104. In FIG. 1A, if article 104 is a glass substrate, then the cylindrical stage 103 suspends article 104 such that the surfaces of article 104 are surrounded by air, which has a lower index of refraction than the index of refraction of article 104. In accordance with Snell's law, when photons are emitted into an internal region of article 104, then a majority and/or a TIR of photons is achieved for image-based feature detection. In some embodiments, the cylindrical stage 103 may support and hold article 104 to surround the surfaces of article 104 with a medium, such as helium, hydrogen, carbon dioxide, water, ethanol, and/or a medium that has a lower index of refraction than the index of refraction of article 104. By the same token, the article 104 may be, as described herein, made of a transparent material, such as glass, acrylic, a metallic material, a diamond based material, or some other material with a higher index of refraction than a medium surrounding the surfaces of article 104.

Although FIG. 1 illustrates a cylindrical stage, it is intended to be an example and is not intended to limit the scope of the concepts described herein. In some embodiments, instead of a cylindrical stage, a rectangular prism shaped stage, a triangular prism shaped stage, and/or a stage configured to support an article in a manner that allows a substantially uniform medium with a lower index of refraction than the index of refraction of the article to surround the surfaces of the article may be utilized. In some embodiments, the cylindrical stage 103 may be made of a substantially transparent material such as a glass and/or a clear plastic. The cylindrical stage 103 may be made of a substantially opaque material, such as a metal, an opaque plastic, wood, and/or some combination thereof.

In some embodiments, apparatus 100 includes photon emitter 106. In some embodiments, photon emitter 106 may be a collimated light source, such as a laser. For instance, the photon emitter 106 may be a red (e.g., 635 nm), a green (e.g., 532 nm), and/or a blue (e.g., 405 nm) laser. The photon emitter 106 may be a laser within a visible range of 400-700 nm, in some instances.

In some embodiments, photon emitter 106 may provide light including: a relatively wide range of wavelengths (e.g., whole spectrum, broad spectrum, ultraviolet-visible, visible, infrared, etc.), a relatively narrow range of wavelengths (e.g., a subdivision of ultraviolet such as UVA, UVB, UVC, etc.; a subdivision of visible such as red, green, blue, etc.; a subdivision of infrared such as near infrared, mid-infrared; etc.), or a particular wavelength (e.g., monochromatic). In some embodiments, the photon emitter 106 may provide light including: a relatively wide range of frequencies (e.g., whole spectrum, broad spectrum, ultraviolet-visible, visible, infrared, etc.), a relatively narrow range of frequencies (e.g., a subdivision of ultraviolet such as UVA, UVB, UVC, etc.; a subdivision of visible such as red, green, blue, etc.; a subdivision of infrared such as near infrared, mid-infrared; etc.), or a particular frequency (e.g., monochromatic). The photon emitter 106 may provide polarized (e.g., linear polarization, circular polarization, etc.) light, partially polarized light, or nonpolarized light; and/or light with different degrees of temporal and/or spatial coherence ranging from coherent light (e.g., laser) to noncoherent light, in some embodiments.

In some embodiments, photon emitter 106 may be used in conjunction with one or more optical components of optical setup 108 to provide light having any of the foregoing qualities. Wavelength filters, for example, may be used in conjunction with photon emitter 106 to provide light including a relatively wide range of wavelengths or frequencies, a relatively narrow range of wavelengths or frequencies, or a particular wavelength or frequency. Polarization filters, for example, may also be used in conjunction with photon emitter 106 to provide light of a desired polarization including polarized light, partially polarized light, or nonpolarized light.

In some embodiments, photon emitter 106 may be configured to direct photons into an internal region of the article 104 to illuminate the article by causing the photons to internally reflect. In some instances, the photon emitter 106 directs photons into an internal region of article 104 from an outer circumferential edge 116 such that the photons are incident at angle (e.g., incidence angle) on a surface of the article 104 (e.g., upper and lower surfaces) that is equal to or greater than a critical angle of the article 104, which is described in greater detail in FIG. 3. It is appreciated that when photons have an incidence angle that is equal to or greater than a critical angle, a total internal reflection and/or a majority of the photons internally reflect within the inner region of article 104. In other words, by achieving or nearly achieving total internal reflection, the photons remain within the internal region of the article 104 by continuously reflecting from surfaces of article 104, which are described in greater detail in FIG. 3. However, if article 104 includes a feature, such as a defect, then the photons scatter at the location of the feature. For example, defects on an upper surface, a lower surface, an outer circumferential edge 116, inner circumferential edge 105, and/or internal to article 104 may cause photons to scatter and emit externally to the article 104. The scattered photons are detected by the optical set up 108 and/or a photon detector array (e.g., photon detector array 302 of FIG. 3) of camera 110. The camera 110 may image the article 104 including the features based on the detected scattered photons. In this way, by internally reflecting photons within article 104, surface features are detectable, especially in transparent articles.

As illustrated in FIG. 1A, in some embodiments, photon emitter 106 may be configured to direct photons into an internal region of article 104 to illuminate the entire article 104 in a single instance, irrespective of the size of article 104. For example, article 104 may be a transparent article with a 2.5 inch diameter that may be entirely illuminated by photon emitter 106. In some instances, article 104 may have a diameter of 3.5 inches, which may be entirely illuminated by photon emitter 106. In this way, article 104 may be imaged in its entirety in a single instance, rather than in a piecemeal manner, which as discussed above creates certain time and article production efficiencies.

In some embodiments, the apparatus 100 includes an optical set up 108. The optical setup 108, in some embodiments, may be configured to manipulate photons emitted from photon emitter 106, and/or photons scattered from the surface defects of article 104. The optical set up 108 may comprise of any number of optical components to manipulate photons/light scattered from features on a surface of the article. For example, the optical set up 108 may include, but is not limited to, lenses, mirrors, and filters (not shown). For instance, the optical set up 108 may comprise a lens (not shown) coupled to a photon detector array (not shown) of camera 110. The lens may be an objective lens, such as a telecentric lens, including an object-space telecentric lens (e.g., entrance pupil at infinity), an image-space telecentric lens (e.g., exit pupil at infinity), or a double telecentric lens (e.g., both pupils at infinity). Coupling a telecentric lens to a photon detector array reduces errors with respect to the mapped position of surface features of articles, reduces distortion of surface features of articles, and/or enables quantitative analysis of photons scattered from surface features of articles, which quantitative analysis includes integration of photon scattering intensity distribution for size determination of surface features of articles.

In some embodiments, the optical set up 108 may include filters (not shown), such filters may include, for example, wave filters and polarization filters. Wave filters may be used in conjunction with photon emitter 106 to provide light including a relatively wide range of wavelengths/frequencies, a relatively narrow range of wavelengths/frequencies, or a particular wavelength/frequency. Polarization filters may be used in conjunction with photon emitter 106 described herein to provide light of a desired polarization including polarized light, partially polarized light, or nonpolarized light.

It is appreciated that the orientation of optical set up 108 in FIG. 1 is illustrative and is not intended to limit the scope of the concepts described herein. In some embodiments, orientation of the optical set up 108 may be dependent on the orientation of camera 110. In some embodiments, the optical set up 108 may be oriented to collect photons scattered from surface features of article 104 at an optimized distance and/or an optimized angle for a maximum acceptance of scattered light and/or one or more types of features. As noted above, such an optimized angle may be the angle between a ray (e.g., a photon or light ray) including the center line axis of the photon detector array to the surface of the article 104 and the normal (i.e., a line perpendicular to the surface of the article 104) at the point at which the ray is extended. The optimized angle may be equal to or otherwise include a scatter angle for one or more types of features, and the scatter angle may be a different angle than the angle of reflection, which angle of reflection is equal to the angle of incidence. For example, the optical set up 108 may be oriented at an optimized angle ranging from 0° to 90°. The optimized angle of 90° represents orientation of the optical set up 108 at a side of the article 104, and an optimized angle of 0° represents orientation of the optical set up directly above the article.

Referring now to camera 110, in some embodiments, it may be coupled to optical set up 108 and communicatively coupled to computer 112. In some embodiments, camera 110 may be configured to capture images of article 104 and transmit the captured images to computer 112 for processing and storage. The camera 110 may be a complementary metal-oxide semiconductor ("CMOS") camera, a scientific complementary metal-oxide semiconductor ("sCMOS") camera, a charge-coupled device ("CCD") camera, or a camera configured for use in feature detection and identification.

In some embodiments, the camera 110 may include a photon detector array (e.g., photon detector array 302 of FIG. 3) configured to collect and detect photons scattered from features on the surface of article 104. The photon detector array (e.g., photon detector array 302 of FIG. 3) may comprise a complementary metal-oxide semiconductor ("CMOS"), a scientific complementary metal-oxide semiconductor ("sCMOS"), or a charge-coupled device ("CCD"), which may be part of camera 110.

In some embodiments, the photon detector array and/or camera 110 may be oriented to collect and detect photons scattered from surface features of article 104 at an optimized distance and/or an optimized angle for a maximum acceptance of scattered light and/or one or more types of features. Such an optimized angle may be the angle between a ray (e.g., a photon or light ray) including the center line axis of the photon detector array to the surface of the article 104 and the normal (i.e., a line perpendicular to the surface of the article 104) at the point at which the ray is extended. The optimized angle may be equal to or otherwise include a scatter angle for one or more types of features, and the scatter angle may be a different angle than the angle of reflection, which angle of reflection is equal to the angle of incidence. For example, photon detector array and/or camera 110 may be oriented at an optimized angle ranging from 0° to 90°. Here, an optimized angle of 90° represents orientation of the photon detector array and/or camera 110 at a side of the article, an optimized angle of 0° represents orientation of the photon detector array or photon detector array directly above the article.

Although FIG. 1A illustrates a single camera with a single photon detector array, it is intended to be illustrative and is not intended to limit the scope of the concepts described herein. In some embodiments, apparatus 100 may comprise a plurality of cameras including a plurality of photon detector arrays. In other embodiments, the apparatus 100 may include a plurality of cameras including a single photon detector array. In further embodiments, the apparatus 100 may include a single camera including a plurality of photon detector arrays.

The apparatus 100 may include a computer 112. The computer 112 may be communicatively coupled to camera 110 to store images of article 104 recorded by camera 110. In some embodiments, the computer 112 may be communicatively coupled to the photon emitter 106 to adjust the angle of photon emitter 106 with respect to article 104. For instance, computer 112 may be configured to: adjust the angle of photon emitter 106 to achieve total internal reflection of photons within article 104, move photon emitter 106 to a distance and/or an angle optimized for inspecting one or more types of features, switch photon emitter 106 on and/or off, and/or switch between modes for emitting photons and not emitting photons.

Computer 112 may also be configured to, but not limited to, mount and unmount article 104 from cylindrical stage 103, position article 104 for inspection, hold or otherwise maintain the position of article 104 on cylindrical stage 103 for illumination and/or inspection, optionally including gradational rotation of article 104 for piecewise inspection. In some embodiments, computer 112 may be configured to insert optical components into the optical setup 108, for example, using a mechanical actuator, position optical components for inspection, adjust optical components (e.g., focus lenses) and/or tune optical components (e.g., piezoelectric-based wavelength filters; piezoelectric-based polarization filters; etc.) for inspection, and/or remove optical components from the optical setup 108.

In some embodiments, the computer 112 may be further configured to identify features of article 104, such as disk defects. For instance, computer 112 may be configured to process photon detector array (e.g., photon detector array 402 of FIG. 4) signals from scattered photons, including pixel interpolation for better accuracy (e.g., 10× better than pixel size) with respect to the position of surface features. In some instances, computer 112 may map or otherwise determine the position of surface features of articles from photon detector array signals or processed photon detector array signals (e.g., photon scattering intensity distributions). The computer 112 may quantitatively and/or qualitatively characterize surface features of articles, in some instances. In some instances, computer 112 may catalog surface features of articles, and determine trends with respect to surface features of articles.

It is appreciated that computer 112 may be a desktop computer, a workstation, a portable device (e.g., a mobile device, a tablet, a laptop, or a smartphone), or some computing device that may be configured to store and perform image based feature detection and inspection.

Figure 1B:
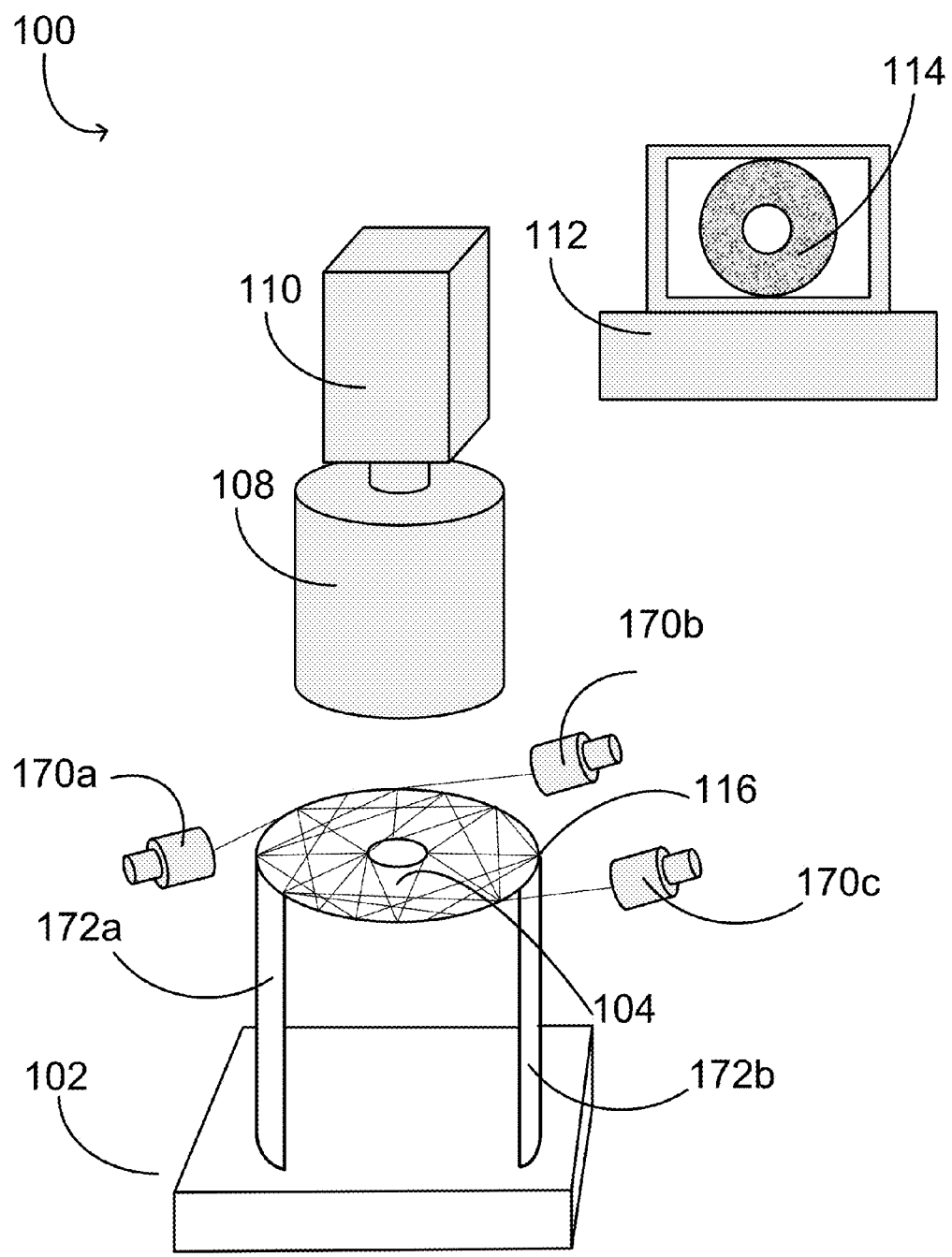

Referring now to FIG. 1B, a schematic illustrating detection of surface features of articles is provided in accordance with an embodiment. The apparatus illustrated in FIG. 1B is substantially similar to the apparatus of FIG. 1A, except that the apparatus includes three photon emitters 170a-170c to illuminate article 104, and includes support beams 172a and 172b to support and hold article 104 for imaging. In some embodiments, photons emitters 170a-170c may be substantially similar to photon emitter 106 of FIG. 1A.

As illustrated in FIG. 1B, photon emitters 170a-170c direct photons into an internal region of article 104 from different locations of the outer circumferential edge 116 of article 104. In some embodiments, three photon emitters 170a-170c or a plurality of photon emitters may be used to internally reflect a uniform density of photons within article 104. In this way, when photons scatter at a location of a surface feature, a uniform density of photons is refracted from the article 104, irrespective of the location of the surface feature. In some instances, photon emitters 170a-170c may be of a light source of the same type. In some instances, photon emitters 170a-170c may be a combination of different light sources, such as a combination of incoherent and coherent light sources, to provide article 104 with a uniform light density. By providing a uniform light density within article 104, greater accuracy in detecting features, image processing (e.g., distinguishing the background in an image compared to a feature of an article, comparing light intensities of features) and classification of features may be achieved.

In some embodiments, photon emitters 170a-170c may be configured to simultaneously direct photons into an inner region of article 104 to cause internal reflection therein. For example, photon emitter 170*a* may be a red laser, photon emitter 170*b* may be a blue laser, and photon emitter 170*c* may be a green laser, which may simultaneously emit photons from different locations of outer circumferential edge 116 into an inner region of article 104. By simultaneously directing photons of different wavelengths (e.g., red, blue, and green), different types of features of article 104 may be detected. In this example, the red laser may be utilized to detect large sized features (e.g., micrometer-sized surface features), the green laser may be utilized to detect medium sized features (e.g., submicrometer-sized surface features), whereas the blue light may be utilized to detected to small sized features (e.g., nanometer-sized surface features).

In some embodiments, photon emitters 170*a*-170*c* may be configured to sequentially emit photons into an inner region of article 104. For example, photon emitter 170*a* may be a red laser, photon emitter 170*b* may be a blue laser, and photon emitter 170*c* may be a green laser. In this example, photon emitters 170*a*-170*c* may be programmed to sequentially direct photons into article 104 in a clockwise direction starting from photon emitter 170*a*. As each photon emitter emits its corresponding set of photons into article 104, the article 104 may be imaged. In this arrangement, different wavelengths of light (e.g., red, blue, and green) may be emitted sequentially to detect different types of features, image the different types of features, and classify the different types of features accordingly. For instance, the red laser may be used to detect and classify large features, whereas the blue and green lasers may be used to detect and classify medium and small features, respectively.

Although the example describes emitting photons from photon emitters 170*a*-170*c* in a clockwise order, it is intended to be an example and it is appreciated that other sequences are within the scope of the concepts described herein. For example, the photon emitters 170*a*-170*c* may emit photons in a counter clockwise sequence or some other user and/or system-defined sequence. It also appreciated that the red, green, and blue wavelengths described above are intended to be illustrative, and other wavelengths of light as described herein may be utilized to cause internal reflection of photons within article 104.

Further, it is appreciated that FIG. 1B illustration of three photon emitters is intended to be an example and is not intended to limit the scope of the concepts described herein. In some embodiments, two photon emitters may be utilized. In further embodiments, 4, 5, 8, 20, and/or 100 photon emitters may be utilized. It is appreciated that any number of photon emitters may be utilized and is within the scope of the concepts described herein.

Referring now to support beams 172*a* and 172*b*, in some embodiments, function in a substantially similar manner as cylindrical stage 103 of FIG. 1A. In FIG. 1B, support beams 172*a* and 172*b* support the article from the outer circumferential edge 116. In some instances, support beams 172*a* and 172*b* may include a latch, a fastener, and/or a clamping system (not shown) secured to the outer circumferential edge 116. Similar to cylindrical stage 103 of FIG. 1A, the support beams 172*a* and 172*b* holds article 104 in a manner that allows a medium with a lower index of refraction than the index of refraction of article 104 to uniformly surround the surfaces of article 104 to facilitate internal reflection of photons within article 104.

Although FIG. 1B illustrates two support beams holding the article for imaging, it is not intended to limit the scope of the concepts described herein. In some embodiments, more than two support beams may be utilized and secured to the outer circumferential edge of the article. For instance, 3, 4, 5, 6, 7, 8, 9, and/or 10 support beams may be secured at different locations on an outer circumferential edge of the article. Further, it is appreciated that the arrangement shown in FIG. 1B is illustrative. In other embodiments, an article may be illuminated with multiple photon emitters as illustrated in FIG. 1B and supported by a stage similar to the cylindrical stage 103 of FIG. 1A. In some embodiments, an arrangement may include one photon emitter to illuminate an article and the article may be supported by support beams such as support beams 172*a* and 172*b* of FIG. 1B.

Figure 1C:
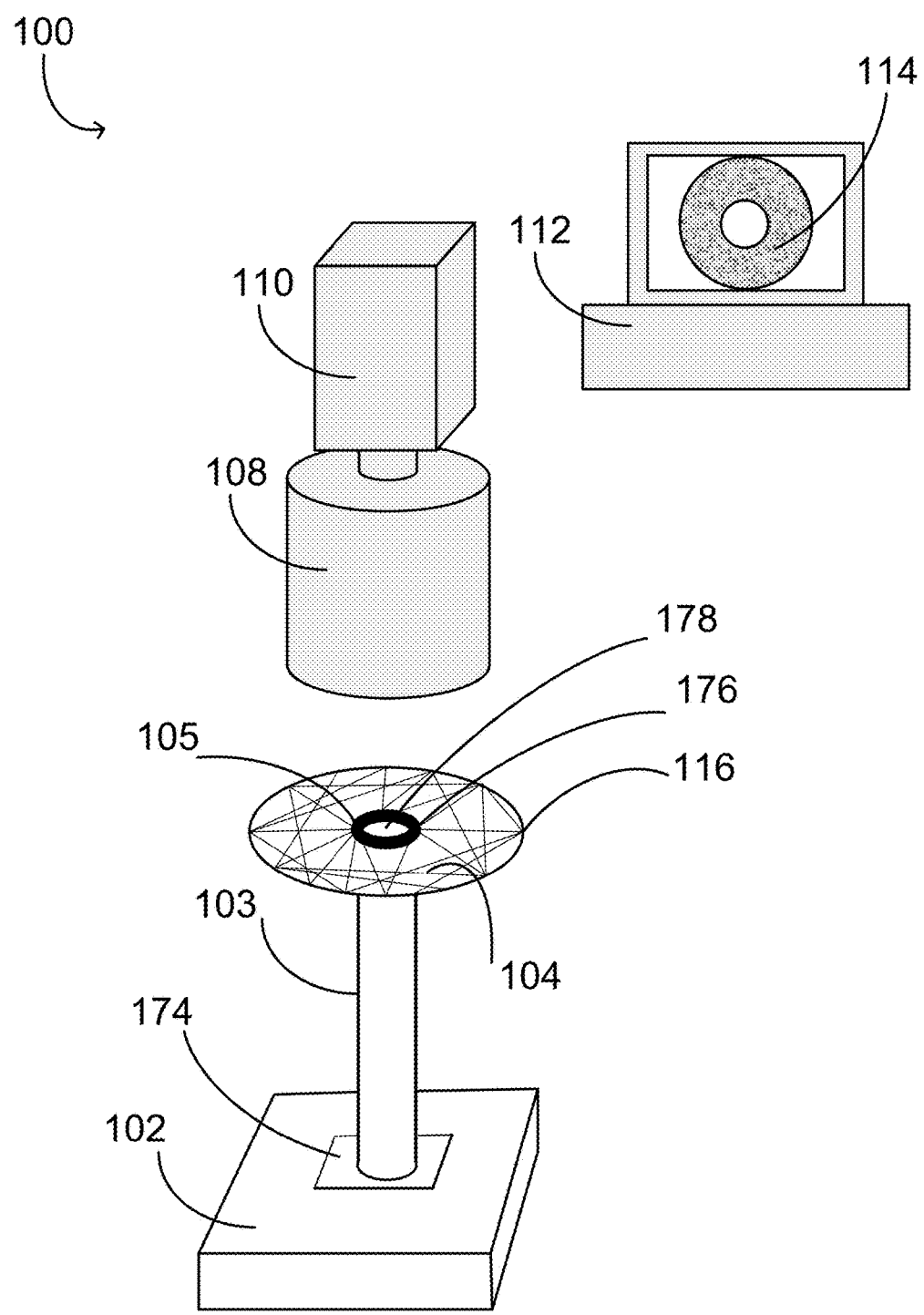

Referring to FIG. 1C, a schematic illustrating detection of surface features of articles is provided in accordance with an embodiment. The apparatus illustrated in FIG. 1C is substantially similar to the apparatus of FIG. 1A, except that stage 102 supports a photon emitter 174. Further, the cylindrical stage 103 supports article 104 and transmits photons from the photon emitter 174 to the inner circumferential edge 105 to cause internal reflection of photons within article 104, which is described in greater detail below.

In some embodiments, photon emitter 174 may be substantially similar to the photon emitter 106 of FIG. 1A and photon emitters 170*a*-170*c* of FIG. 1B. Cylindrical stage 103 includes a clamp 176 (depicted as a bold circle near to or on the inner circumferential edge 105) to secure and hold article 104 for imaging. In some embodiments, clamp 176 may be a rubber clamp, a metal clamp, a plastic clamp, a glass clamp, a wooden clamp and/or some combination thereof. In some embodiments, clamp 176 may be a F-clamp, a C-clamp, and/or a clamping/fastening system that holds article 104 securely for imaging.

Figure 2A:
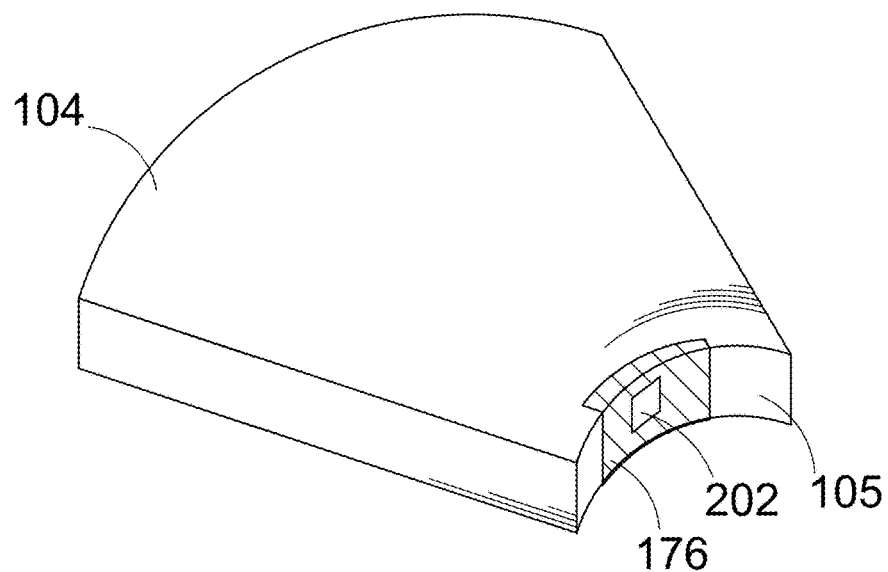
FIGS. 2A-2B show a sectional perspective of an article and a clamp including an inlet in accordance with some embodiments.

After photon emitter 174 emits photons, the cylindrical stage 103 transmits the photons from the photon emitter 174 to the clamp 176. In order to direct photons into an internal region of article 104, the clamp 176 includes an inlet near or at the inner circumferential edge 105 of the article 104, as shown in FIG. 2A. FIG. 2A illustrates an inlet 202 and/or a cut-out in the clamp 176 that allows photons to be directed into article 104 and cause the photons to internally reflect. In some embodiments, the clamp 176 and the inlet 202 are on the inner circumferential edge 105. In some embodiments, the clamp 176 and the inlet 202 are near the inner circumferential edge 105, such as, a portion of the inlet is a fraction of a millimeter, a millimeter, a couple millimeters or several millimeters away from the inner circumferential edge 105. By leaving a certain amount of distance between the inlet 202 from the inner circumferential edge 105, the inner circumferential edge 105 may interface with a medium that has a lower index of refraction, such as air, than the index of refraction of article 104. In this way, a majority and/or a total internal reflection of the photons may be achieved, which is described in greater detail in FIG. 3, and thus, features of article 104 may be detected and imaged.

In some embodiments, cylindrical stage 103 may include lenses and/or mirrors to direct and reflect the photons toward an inlet (e.g., inlet 202 of FIG. 2A) of clamp 176. In some embodiments, the cylindrical stage 103 includes clamp 176 that includes an inlet as described herein, and further include a cap (not shown) that is positioned to cover the center hole 178 of article 104. In such an arrangement, photons may be emitted from photon emitter 174 and travel upward toward an inlet (e.g., inlet 202 of FIG. 2A) of clamp 176. However, it is appreciated that in such an arrangement some of the photons may travel toward the center hole 178. As such, a cap (not shown) may be used to block the photons from being recorded and imaged by camera 110, and ensures that only features of article 104 are recorded and imaged.

It is appreciated that the illustration in FIG. 1C of clamp 176 being secured to the entire inner circumferential edge 105 is intended to be an example, and is not intended to limit the scope of the concepts described herein. In some embodiments, the clamp 176 may be secured to some portions of the inner circumferential edge 105. Further, it is appreciated that the discussion of clamp 176 including one inlet (e.g., inlet 202 of FIG. 2A) is illustrative, and that clamp 176 may include more than one inlet, such as 2, 3, 4, 5, 6, 7, 8, 9, and/or 10 inlets, arranged at or near different locations of the inner circumferential edge 105.

Figure 1D:
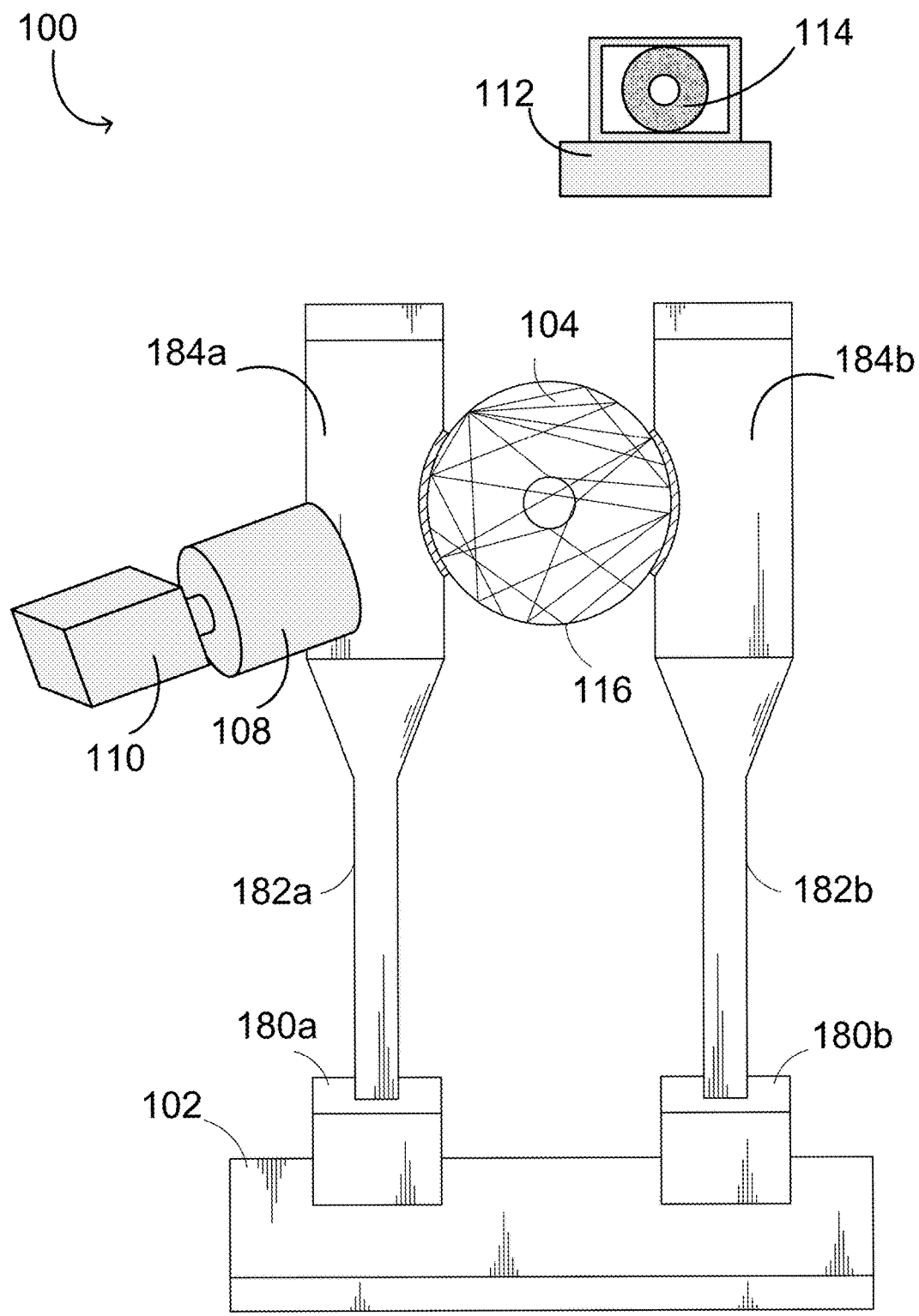

Referring to FIG. 1D, a schematic illustrating detection of surface features of articles is provided in accordance with an embodiment. The apparatus of FIG. 1D is substantially similar to the apparatus of FIG. 1A-1C with a few exceptions. In FIG. 1D, stage 102 supports photon emitters 180a-180b, which are interfaced with support beams 182a-182b. The support beams 182a-182b support clamps 184a-184b, which hold article 104 for imaging.

It is appreciated that photon emitters 180a-180b are substantially similar to photon emitter 106 of FIG. 1A, photon emitters 170a-170c of FIG. 1B, and photon emitter 174 of FIG. 1C. Further, support beams 182a-182b may function in a substantially similar manner as cylindrical stage 103 of FIG. 1C, except that the support beams 182a-182b are positioned in alignment with the outer circumferential edge 116 of article 104. Clamps 184a-184b also function in a substantially similar manner as clamp 176 of FIG. 1C, except that clamps 184a-184b hold the article from the outer circumferential edge 116.

Figure 2B:
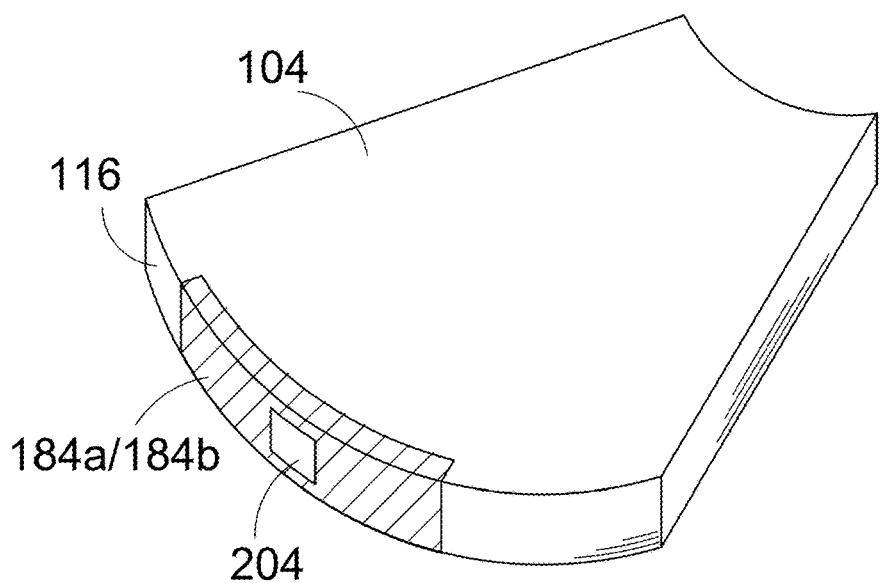

Similar to FIG. 1C, after photon emitters 180a-180b emit photons, the support beams 182a-182b transmit the photons to the clamps 184a-184b, respectively. Similar to clamp 176 of FIG. 1C, clamps 184a-184b include inlets near or at the outer circumferential edge 116 that allow photons to be directed into article 104 and cause the photons to internally reflect. For example, clamps 182a-184b may include an inlet 204 as illustrated in FIG. 2B. In some embodiments, support beams 182a-182b and/or clamps 184a-184b may include lenses and/or mirrors to direct photons toward an inlet near and/or on the outer circumferential edge 116 to direct photons into an internal region of article 104.

Although FIG. 1D shows two support beams 182a-182b transmitting photons from photon emitters 180a-180b to clamps 184a-184b, respectively, it is intended to be illustrative and not intended to limit the scope of the concepts described herein. In some embodiments, one out of the two support beams 182a-182b may interface with a photon emitter and transmit the photons for internal reflection within article 104. It is further appreciated that clamps 184a-184b may include one or more inlets positioned in different location near or at the outer circumferential edge 116, in some embodiments. It is further appreciated that in some arrangements, one out of the two clamps 184a and 184b may include one or more inlets near or at outer circumferential edge 116 to direct photons into an internal region of article 104.

Figure 1E:
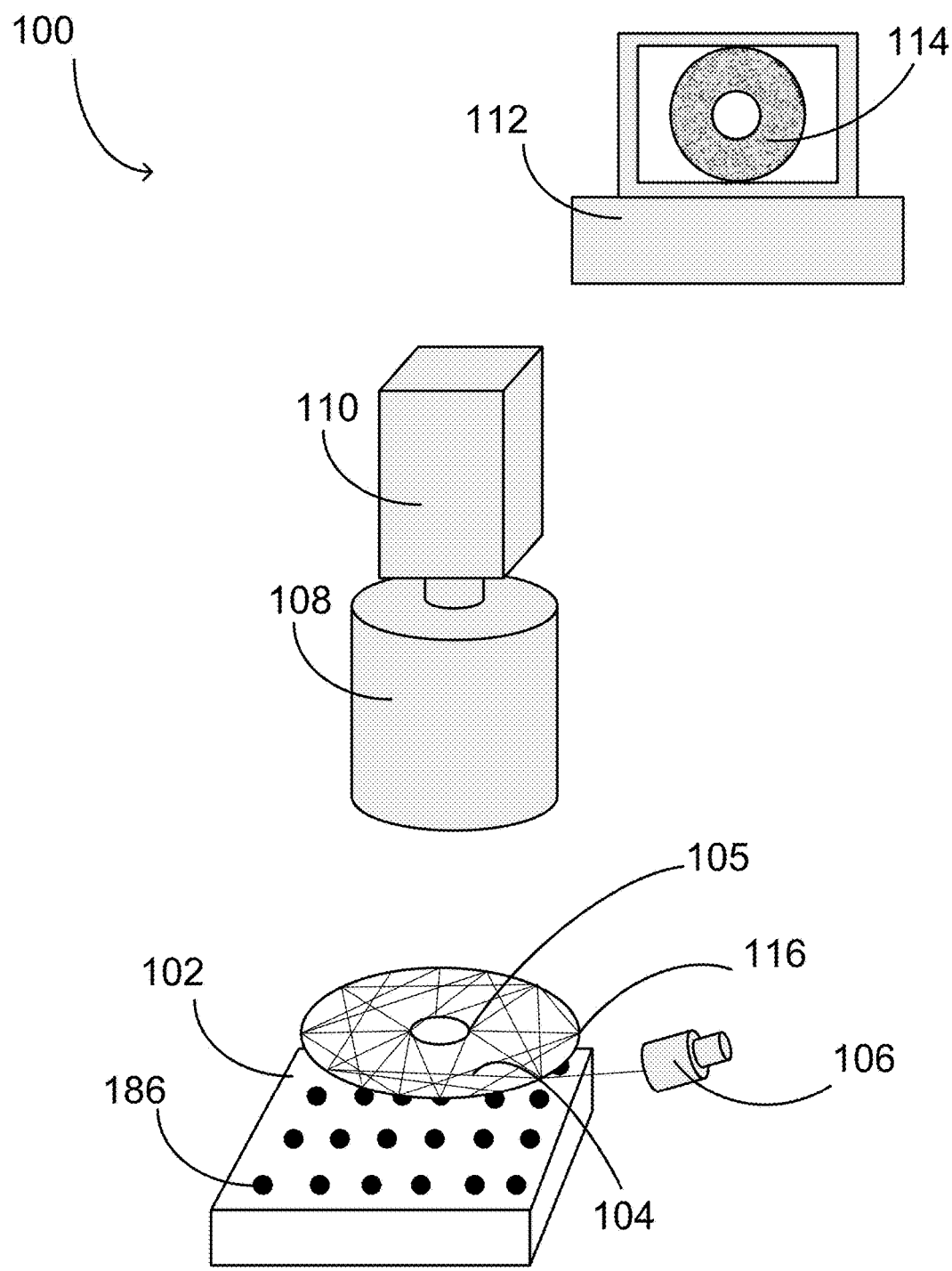

Referring to FIG. 1E, a schematic illustrating detection of surface features of articles is provided in accordance with an embodiment. The apparatus of FIG. 1E is substantially similar to the apparatus of FIG. 1A-1D, except that article 104 is supported by stage 102 instead of cylindrical stage and/or support beams. Similar to cylindrical stage 103 of FIG. 1A, stage 102 supports article 104 in a manner that allows a substantially homogeneous medium with a lower index of refraction than the index of refraction of article 104 to surround the surfaces (e.g., upper surface, lower surface, inner and/or outer circumferential edges) of article 104. For instance, if article 104 is a glass substrate, then stage 102 suspends the article 104 in air. In this way, article 104 is surrounded by air which is a medium that has a lower index of refraction than article 104. When photons are emitted from photon emitter 106 into the article 104 from the outer circumferential edge 116, then a majority and/or a TIR of photons is achieved for image-based feature detection.

In order to suspend article 104, the surface of stage 102 is perforated by multiple surface holes 186. Further stage 102 includes a fan and/or an air blower (not shown) that blows air upwards and into the surface holes 186. When the air from the surface holes 186 contacts a lower surface of article 104, it causes the article 104 to be suspended in air. In other words, an air cushion is created in between the surface of stage 102 and the lower surface of article 104, which allows the article 104 to be surrounded by air, a medium with a lower refraction index than the article 104.

Although FIG. 1E illustrates a single photon emitter to illuminate an internal region of the article, it is appreciated that more than one photon emitter may be used in some arrangement. For instance, as described in FIG. 1B, multiple photon emitters may be used and arranged in different location to emit photon from an inner and/or outer circumferential edge into an internal region of article 104.

Figure 3:
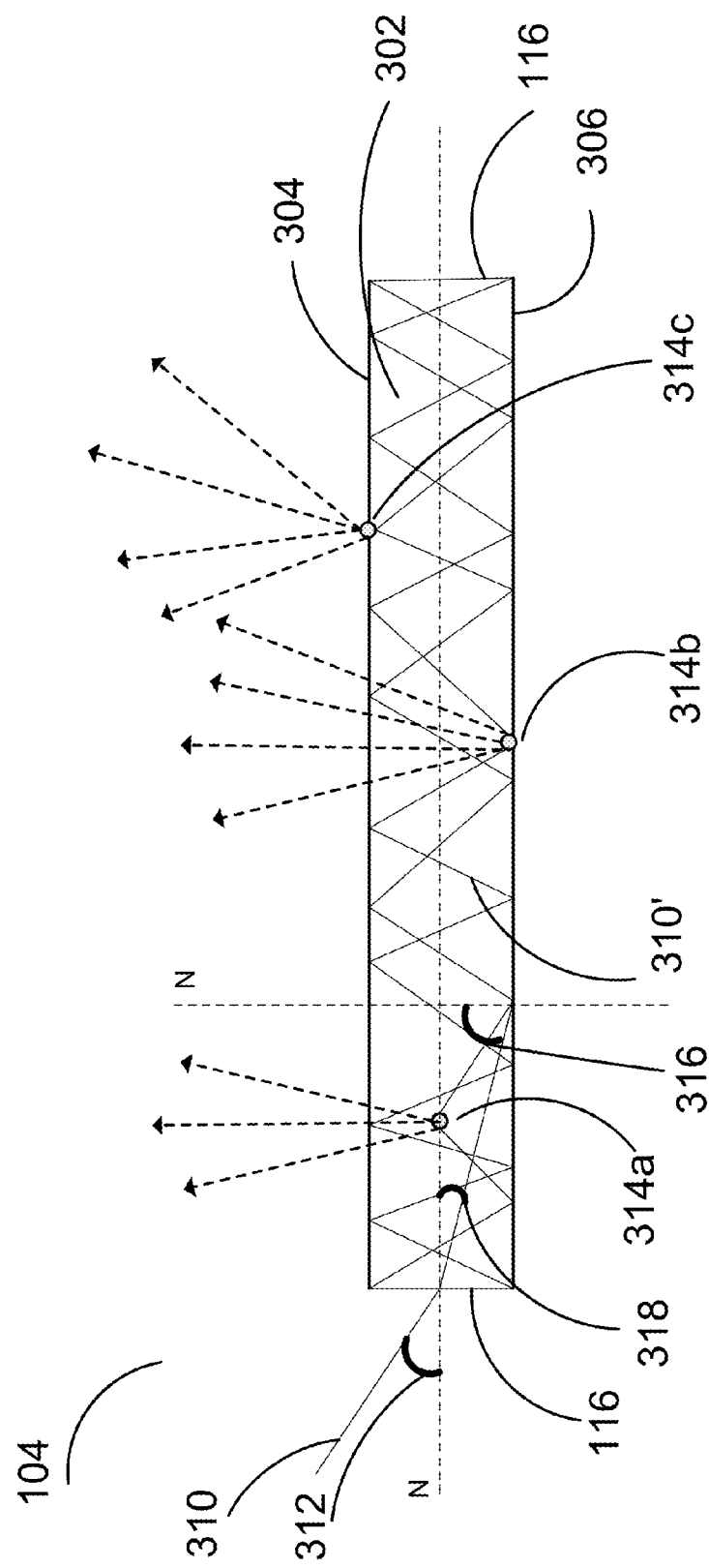
FIG. 3 shows a cross-sectional perspective of an article inspected for surface features in accordance with an embodiment.

Referring to FIG. 3, a cross-sectional perspective of article 104 being inspected for surface features is shown in accordance with an embodiment. As illustrated in FIG. 3, article 104 comprises of an inner region 302, an upper surface 304, a lower surface 306, and circumferential outer edges 116. The circumferential outer edges 116 connect the lower surface 306 to the upper surface 304, thereby creating the internal region 302. Although FIG. 3 illustrates upper surface 304 and lower surface 306 as linear surfaces, it is appreciated that the upper surface 304 and the lower surface 306 may be curved surfaces in some embodiments.

As illustrated in FIG. 3, a beam of photons 310 is projected from a photon emitter, such as photon emitters described in FIGS. 1A-1E. The beam of photons 310 is projected into the inner region 302 from the circumferential outer edge 116, such that the photons have an incidence angle 316 that produces an angle of refraction greater than 90 degrees at the upper surface 304 and/or lower surface 308. It is appreciated that in view of Snell's law and the theory of total internal reflection, that once an angle of refraction of a photon is greater than 90 degrees at a surface (e.g., upper surface 304 and/or lower surface 308), the photon will not refract through the surface. Instead, the photon will reflect off the surface. When this happens, total internal reflection occurs.

It is further appreciated that total internal reflection is achieved when the photon beam 310 directs photons at the circumferential outer edge 116 at an angle 312 such that the photons have an incidence angle 316 greater than a critical angle. The critical angle is the angle of incidence that provides an angle of refraction of 90 degrees. The determination of a critical angle is dependent upon the index of refraction of mediums on either side of upper surface 304 and either side of lower surface 306. Specifically, if the mediums on either side of upper surface 304 and the lower surface 306 have a lower index of refraction than the index of refraction of article 104, then total internal reflection and/or nearly total internal reflection of photons within the internal region 302 may be achieved.

In an illustrative example, if article 104 is a glass substrate and the medium surrounding upper surface 304 and lower surface 306 is air, then the glass substrate may have an index of refraction of about 1.52 and the air surrounding the upper surface 304 has an index of refraction of about 1.0. Because article 104 has a greater index of refraction than air, the photons 310' will internally reflect when the photons 310' are in contact with upper surface 304 and the lower surface 306 at an angle of incidence 316 greater than the critical angle. In this example, the critical angle is about 41.1°, which is calculated based on Snell's law.

Specifically, the critical angle is calculated as follows: $\theta_{crit}$=arcsin ($n_r/n_i$). Here, $\theta_{crit}$ is a critical angle based on the arcsine of a ratio between indices of refraction of the refractive medium $n_r$, which is air in this example, and the incident medium which is article 104 in this example. As such, the critical angle, as noted above, is 41.1° (e.g., arcsin (1.0/1.52)).

It is further appreciated that in order to achieve an angle of incidence 316 as described herein for photons 310' with the surfaces of article 104 (e.g., upper surface 304 and lower surface 306), the beam of photons 310 are directed from an outer circumferential edge 116 at an angle 312. For example, if article 104 is a transparent glass substrate surrounded by water at the upper surface 304, then the critical angle is 61 degrees. To achieve total internal reflection, refraction angle 312 may be less than 29 degrees, thereby resulting in photons 310' that have an incidence angle greater than 61 degrees at surface 304. As such, in this example, the angle 312 may be an angle, such as 45 degrees, that results in a refraction angle 312 that is less than 29 degrees. It is appreciated that angle 312 is based on Snell's law and the index of refraction of the medium surrounding article 104 (e.g., air) and the index of refraction of article 104. In some different arrangements, the angle 312 may be adjusted based on (1) index of refraction of the medium surrounding the article 104 and the index of refraction of the article 104 when the beam of photons 310 is incident on the outer circumferential edge 116 and (2) the critical angle of the mediums. For example, angle 312 may be 20°, 30°, 40°, 50°, 60°, 80°, 90°. In some embodiments, the angle 312 may be at least 0°, 5°, 10°, 15°, 20°, 25°, 30°, 35°, 40°, 45°, 50°, 55°, 60°, 65°, 70°, 75°, 80°, or 85°. In some embodiments, the angle 312 may be no more than 90°, 85°, 80°, 75°, 70°, 65°, 60°, 55°, 50°, 45°, 40°, 35°, 30°, 25°, 20°, 15°, 10°, or 5°. Combinations of the foregoing may also be used to describe the angle 312. For example, in some embodiments, the angle 312 may be at least 0° and no more than 30° (i.e., between 0° and 30°), such as at least 10° and no more than 40° (i.e., between 10° and 40°), for example, at least 20° and no more than 50° (i.e., between 20° and 50°).

When the beam of photons 310 penetrates through to the inner region 302, the photons 310' reflect from the upper surface 304 and the lower surface 308 at an angle greater than 90 degrees, which results in total internal reflection of photons 310'. It is appreciated that photons 310' reflect within the upper surface 304 and lower surface 306 indefinitely without exiting article 104 because article 104 is surrounded by a medium (e.g., air) that has a lower index of refraction than article 104. However, when photons 310' reflection path is obstructed by a surface feature, such as surface features 314a, 314b, and 314c, the photons 310' scatter (depicted as dashed arrows) and illuminate a location of the feature. A photon detector array as described herein may detect the photons scattered from article 104, and may be further imaged, mapped, and/or analyzed by a camera and/or a computing device as described in FIGS. 1A-1E.

Although FIG. 3 illustrates emitting photons from an outer circumferential edge 116 into an internal region 302, it is intended to be an example and is not intended to limit the scope of the concepts described herein. In some embodiments, photons may be emitted from an inner circumferential edge as described in FIG. 1C. Further, it is appreciated that the illustration of the outer circumferential edge 116 as a straight edge is intended to be illustrative, and is not intended to limit the scope of the concepts described herein. In some embodiments, the inner and/or outer circumferential edges described herein may be straight edges, beveled edges, and/or curved edges.

FIG. 4 provides a schematic for detection of surface features of an article, illustrating a close-up, cross-sectional view of an apparatus including an optical setup and a photon detector array. As shown, article 104 comprises a surface 400 and at least a surface feature 406. Photons may be scattered by surface feature 406 and collected and detected by a combination by an optical set up 108 including a lens coupled to a photon detector array 402 of camera 110, which combination may be positioned at a distance and/or an angle for an optimum acceptance of photons (e.g., maximum acceptance of photons with minimum background noise) scattered from one or more types of features. The optical setup 108, which may comprise a telecentric lens, may collect and focus the photons scattered from the surface feature 406 onto one or more pixel sensors 404 of photon detector array 402, which one or more pixel sensors may each comprise a photon detector coupled to an amplifier (e.g., CMOS/sCMOS-based photon detector array). The one or more pixel sensors 404, each of which corresponds to a particular, fixed area of an article's surface and a pixel in a map of the article's surface features, may provide one or more signals to a computer or equivalent device (e.g., computer 112 of FIGS. 1A-1E) for mapping or otherwise determining the position of the surface feature 406. FIG. 7A provides an illustrative example of a close-up image of the map of surface features provided in FIG. 6, which, in turn, is in an illustrative example of a close-up image of the map of surface features provided in FIG. 5. The computer or equivalent device may subsequently use pixel interpolation for further mapping the surface feature 406. FIG. 7B provides an illustrative example of a pixel-interpolated image of a surface feature, such as a surface feature from FIG. 7A. Although FIGS. 5-6 and FIGS. 7A-7B depict images of a magnetic medium, it is appreciated that the depictions are illustrative and are not intended to limit the scope of the concepts described herein. It is appreciated that appreciated that the imaging, and mapping, pixel interpolation illustrated in FIGS. 5-6 and FIGS. 7A-7B may be used for articles in different stage of manufacture, such as a transparent article as described herein.

In some embodiments, the combination of the optical set up 108, photon detector array 402, and camera 110 of FIG. 4 and computer 112 of FIGS. 1A-1E may be configured to detect and/or map surface features of articles. In some instances, the surface features are nanometer-sized (i.e., admits of nm units as measured) or smaller in their smallest dimension (e.g., length, width, height, or depth, depending on the surface feature), which surface features may be smaller than the wavelength of photons emitted from a photon emitter (e.g., photon emitters FIGS. 1A-1E) of the apparatus. In some embodiments, micrometer-sized (i.e., admits of μm units as measured) or larger surface features may be detected and mapped, such as surface features smaller than 500 nm, 250 nm, 200 nm, 150 nm, 125 nm, 110 nm, 100 nm, 90 nm, 80 nm, 70 nm, 60 nm, 50 nm, 40 nm, 30 nm, 20 nm, 10 nm, or 1 nm (10 Å) in their smallest dimension, or even smaller, such as surface features of articles smaller than 9 Å, 8 Å, 7 Å, 6 Å, 5 Å, 4 Å, 3 Å, 2

Å, or 1 Å in their smallest dimension. In view of the foregoing, and in some embodiments, for example, the apparatus described herein may be configured for detecting and/or mapping surface features of articles, wherein the surface features are between 0.1 nm and 1000 nm, such as between 0.1 nm and 500 nm, including between 0.1 nm and 250 nm, and further including between 0.1 nm and 100 nm, and even further including between 0.1 nm and 80 nm.

In some embodiments, nanometer-sized (i.e., admits of nm units as measured) or smaller in their smallest dimension (e.g., length, width, or height) surface features may be detected and/or mapped by the optical set up 108 and/or photon detector 402. For example, subsurface particles smaller than 125 nm, such as smaller than 100 nm, including smaller than 80 nm, and further including smaller than 10 nm in their smallest dimension may be detected by photon detector array 402 and/or mapped by a computer, such as computer 112 of FIGS. 1A & 1B. Detecting and/or mapping surface and/or subsurface particles down to the level of 10 nm in height is important for hard disks of hard disk drives, as particles greater than 10 nm in height (e.g., from the surface) may corrupt the spacing between the hard disk and the read-write head of a hard disk drive. In some embodiments, for example, the photon detector array 402 may be configured for detecting, and a computer described herein for mapping, surface and/or subsurface particles as small as or smaller than 4 nm in height.

In some embodiments, surface and/or subsurface defects including scratches (e.g., circumferential scratches) that are micrometer-sized (i.e., admits of μm units as measured) or smaller, such as nanometer-sized (i.e., admits of nm units as measured) or smaller, such as angstrom-sized (i.e., admits of Å units as measured) or smaller, in their smallest dimension (e.g., length, width, or depth) may be detected by photon detector array 402, and then mapped by a computer described herein. With respect to micrometer-sized scratches, 1 μm to 1000 μm in length, which may be significantly longer than the wavelength of photons emitted from a photon emitter of the apparatus may be detected. In some instances, scratches smaller than 1000 μm, such as smaller than 500 μm, including smaller than 250 μm, further including smaller than 100 μm, and even further including smaller than 50 μm in scratch length may be detected by photon detector array 402.

With respect to nanometer-sized scratches, 1 nm to 500 nm in scratch width may be detected by photon detector array 402. In some instances, scratches smaller than 500 nm, such as smaller than 250 nm, including smaller than 100 nm, further including smaller than 50 nm, and even further including smaller than 15 nm in scratch width may be detected. Surprisingly, due to a high level of spatial coherence, the photon detector array 402 may be configured for detecting and/or mapping angstrom-sized scratches with respect to scratch depth. In some embodiments, for example, the photon detector array 402 may be configured for detecting scratches smaller than 50 Å, such as smaller than 25 Å, including smaller than 10 Å, further including smaller than 5 Å, and even further including smaller than 1 Å (e.g., 0.5 Å) in scratch depth. For example, scratches smaller than 500 μm in length, smaller than 100 nm in width, and smaller than 50 Å in depth may detected.

Once the photon detector array 402 detects one or more surface features as described herein, camera 110 may image the article 104 and provide the image to an apparatus, such as apparatus 100 of FIGS. 1A and 1B to accurately and/or precisely map or otherwise determine the position of a feature on an article's surface (e.g., FIGS. 6A (top) and 6B (top) provide illustrative examples of determining a position of a feature on an article's surface). With respect to accuracy, the apparatus may be operable to map or otherwise determine the position of a feature on an article's surface within a micrometer-sized (i.e., admits of μm units as measured) radius or better. In some embodiments, for example, the apparatus may be operable to accurately map or otherwise determine the position of a feature on an article's surface within a radius of 100 μm, 90 μm, 80 μm, 70 μm, 60 μm, 50 μm, 40 μm, 30 μm, 20 μm, 10 μm, 9 μm, 8 μm, 7 μm, 6 μm, 5 μm, 4 μm, 3 μm, 2 μm, or 1 μm, or better. In some embodiments, for example, the apparatus may be operable to accurately map or otherwise determine the position of a feature on an article's surface within a radius ranging from 1 μm to 100 μm, such as from 1 μm to 50 μm, including from 1 μm to 30 μm, and further including from 5 μm to 10 μm.

In addition to accurately and/or precisely mapping or otherwise determining the position of a feature on a surface of an article, the apparatus described herein may be operable to accurately and/or precisely determine the photon scattering intensity distribution (e.g., FIGS. 6A (bottom) and 6B (bottom) provide some illustrative examples) of the feature on the surface of the article. Such a photon scattering intensity distribution may be used characterize a surface feature of an article both quantitatively and qualitatively.

With respect to quantitative characterization of a surface feature of an article, mathematical integration of a photon scattering intensity distribution provides the size (e.g., volume) of the surface feature of the article. Quantitative characterization of a surface feature of an article may further include a determination of surface feature position on the article as described herein. Quantitative characterization may even further include the total number of surface features per article, or the number of surface features per unit area per article, as well as the number of each type of surface feature on the article. Such characterization information may be cataloged across a plurality of articles and be used to correct manufacturing trends should such features include surface and/or subsurface defects that might degrade the performance of the article.

With respect to qualitative characterization of a surface feature of an article, qualitative characterization may include a determination of the type of surface feature (e.g., particle, stain, scratch, void, etc.) of the article, which determination may be effected by, but is not limited to, analysis of photon scattering intensity distributions. Qualitative characterization may further include distinguishing between surface features known to differentially scatter photons with respect to wavelength; a polarization filter may be used to distinguish between surface features known to differentially scatter photons with respect to polarization; a coherence filter may be used to distinguish between surface features known to differentially scatter photons with respect to coherence; and a phase filter or waveplate may be used to distinguish between surface features known to differentially scatter photons with respect to phase. In some embodiments, for example, qualitative characterization of one or more surface features of an article may comprise contrasting photon-scattering information in the effective absence of one of the foregoing filters with photon-scattering information using one or more of the foregoing filters or contrasting a first surface features map produced in the effective absence of one of the foregoing filters with a second surface features map (or a plurality of surface features maps) produced using one or more of the foregoing filters. Along with quantitative characterization information, such qualitative characterization information may be cataloged across a plurality of articles and be used to correct manufacturing trends should such features include surface and/or subsurface defects that might degrade the performance of the article.

The apparatus described herein may be configured to process or inspect articles at a rate greater than or commensurate with the rate at which the articles or workpieces thereof are produced. In some embodiments, for example, the apparatus may be configured to process or inspect articles at a rate of at least 1, 2, 3, 4, 5, 6, 7, 8, 9, 10, 12, 14, 16, 18, or 20 article(s) per second, which rate may be commensurate with the rate at which the articles or workpieces thereof are produced. In some embodiments, for example, the apparatus may be configured to process or inspect articles at a rate of no more than 20, 18, 16, 14, 12, 10, 9, 8, 7, 6, 5, 4, 3, 2, or article(s) per second, which rate may be commensurate with the rate at which the articles or workpieces thereof are produced. Combinations of the foregoing may also be used to describe the rate at which the articles or workpieces thereof are processed or inspected by the apparatus. In some embodiments, for example, the apparatus may be configured to process or inspect at least 1 and no more than 20 articles per second (e.g., between 1 and 20 articles per second), such as at least 1 and no more than 10 articles per second (e.g., between 1 and 10 articles per second), including at least 1 and no more than 5 articles per second (e.g., between 1 and 5 articles per second). Processing or inspecting articles at rates greater than or commensurate with the rate at which the articles or workpieces thereof are produced is a function of many features of the apparatus described herein, including, but not limited to, photon emitters and/or articles that need not be moved (e.g., for scanning) during processing or inspecting. For example, an article such as a transparent substrate of a hard disk drive need not be rotated during processing or inspecting. As such, the apparatus may be configured to hold an article stationary while emitting photons onto the surface of the article.

As such, provided herein is an apparatus comprising a stage configured to hold an article, and a photon emitter configured to emit photons into an internal region of the article and causing the photons to internally reflect. In some embodiments, the photons scatter at a location of a feature of the article. The apparatus further comprises a photon detector array configured to detect photons scattered from the article, in some embodiments.

In some embodiments, the photon emitter is configured to direct photons into the internal region from an outer circumferential edge and/or an inner circumferential edge of the article. In some embodiments, the photon emitter is configured to direct photons into the internal region from the outer circumferential edge and/or the inner circumferential edge at an angle that produces an angle of refraction greater than 90 degrees.

In some embodiments, the apparatus further comprises another photon emitter configured to emit photons into the internal region of the article. The photon emitter and the another photon emitter emit photons from different locations of an edge of the article, in some embodiments. In some embodiments, the stage includes a clamp at a first end configured to hold the article, and the stage is configured to transmit photons emitted from the photon emitter positioned at or near a second end of the stage to the clamp. In some embodiments, the clamp includes an inlet near or at an edge of the article, and the clamp is configured to provide photons emitted from the photon emitter into the internal region of the article through the inlet to the edge of the article.

In some embodiment, the apparatus further comprises a camera including the photon detector array. The camera is configured to image the entire article, in some embodiments. In some embodiments, the camera is selected from the group consisting of a complementary metal-oxide semiconductor ("CMOS") camera and a scientific complementary metal-oxide semiconductor ("sCMOS") camera.

Also, provided herein is an apparatus, comprising: a first photon emitter configured to emit photons into an article from a circumferential edge of the article, and a photon detector array configured to detect photons scattered from features of the article.

In some embodiments, the first photon emitter is configured to emit photons into an internal region of the article from the circumferential edge at an angle that produces an angle of refraction that is equal to or greater than a critical angle of the article. In some embodiments, the apparatus further comprises a second photon emitter configured to direct photons into an internal region of the article, wherein the first and second photon emitters emit photons from different locations of the circumferential edge. The first photon emitter is configured to emit photons of a first wavelength and the second photon emitter is configured to emit photons of a second wavelength to allow the photon detector array to detect different types of surface features of the article, and the first and second wavelengths are different, in some embodiments.

In some embodiments, the apparatus further comprises a stage configured to hold the article and further configured to transmit photons emitted from the photon emitter to the circumferential edge of the article. The stage includes a clamp configured to fasten to the edge of the article, and the clamp includes an inlet configured to provide photons emitted from the photon emitter to the edge of the article, in some embodiments.

In some embodiments, the apparatus further comprises a camera including the photon detector array. The camera is configured to image the entire article, and the camera is selected from the group consisting of a complementary metal-oxide semiconductor ("CMOS") camera and a scientific complementary metal-oxide semiconductor ("sCMOS") camera, in some embodiments.

Further provided herein is a method, comprising: emitting photons into an article from an edge of the article, internally reflecting the photons within the article, scattering the photons at a feature of the article, and detecting the scattering with a photon detector array, in some embodiments.

In some embodiments, the method further comprises prior to emitting photons, mounting the article on a stage. Emitting photons includes transmitting the photons via the stage to the edge of the article, in some embodiments. In some embodiments, emitting photons includes emitting photons into the article via an inlet of a clamp of the stage fastened at the edge of the article. In some embodiments, emitting the photons includes emitting photons into the article from the edge at an angle that produces an angle of refraction greater than 90 degrees.

In some embodiments, the method further comprises sequentially emitting photons of different wavelengths from different photon emitters. The method further comprises simultaneously emitting photons from different photon emitters into the article, in some embodiments. In some embodiments, the different photon emitters emit photons from different locations on the edge of the article.

While the embodiments have been described and/or illustrated by means of particular examples, and while these embodiments and/or examples have been described in considerable detail, it is not the intention of the applicant(s) to restrict or in any way limit the scope of the embodiments to such detail. Additional adaptations and/or modifications of the embodiments may readily appear to persons having ordinary skill in the art to which the embodiments pertain, and, in its broader aspects, the embodiments may encompass these adaptations and/or modifications. Accordingly, departures may be made from the foregoing embodiments and/or examples without departing from the scope of the concepts described herein, which scope is limited only by the following claims when appropriately construed.

What is claimed is:

1. An apparatus comprising:
a stage configured to hold an article;
a first photon emitter configured to emit photons, having a first wavelength, to an inlet of a clamp into an internal region of the article and causing the photons to internally reflect, wherein the inlet is positioned on an inner circumferential edge of the article;
a second photon emitter configured to emit photons having a second wavelength into the internal region of the article and causing the photons to internally reflect;
a photon detector array configured to detect photons emitted from the first and second photon emitters that are scattered from features of the article; and
a computing device configured to detect features of the article having a first size based on the scattered photons having the first wavelength emitted from the first photon emitter and features of the article having a second size based on the scattered photons having the second wavelength emitted from the second photon emitter.

2. The apparatus of claim 1, wherein the first and second photon emitters are further configured to direct photons into the internal region from an outer circumferential edge and/or an inner circumferential edge of the article.

3. The apparatus of claim 2, wherein the first and second photon emitters are further configured to direct photons into the internal region from the outer circumferential edge and/or the inner circumferential edge at an angle that produces an angle of refraction greater than 90 degrees.

4. The apparatus of claim 1, wherein the first photon emitter and the second photon emitter emit photons from different locations of an edge of the article.

5. The apparatus of claim 1, wherein the stage includes first and second clamps at a first end configured to hold the article; and wherein the stage is configured to transmit photons emitted from the first and second photon emitters positioned at or near a second end of the stage to the first and second clamps.

6. The apparatus of claim 5, wherein the first and second clamps each includes an inlet near or at an edge of the article, wherein the first clamp is configured to provide photons emitted from the first photon emitter into the internal region of the article through the inlet of the first clamp to the edge of the article, wherein the second clamp is configure to provide photons emitted from the second photon emitter into the internal region of the article through the inlet of the second clamp to the edge of the article.

7. The apparatus of claim 1 further comprising:
a camera including the photon detector array;
wherein the camera is configured to image the entire article, and
wherein the camera is selected from the group consisting of a complementary metal-oxide semiconductor ("CMOS") camera and a scientific complementary metal-oxide semiconductor ("sCMOS") camera.

8. The apparatus of claim 1, wherein the features of the article having the first size are micrometer-sized features, wherein the features of the article having the second size are submicrometer-sized features.

9. An apparatus comprising:
a photon emitter configured to emit photons from an inlet of a clamp into an article from a circumferential edge of the article, wherein the photon emitter is configured to emit photons into an internal region of the article from the circumferential edge at an angle that produces an angle of refraction that is equal to or greater than a critical angle of the article, and wherein the inlet is positioned on an inner circumferential edge of the article; and
a camera comprising a photon detector array configured to detect photons scattered from features of the article, wherein the camera is configured to image the entire article in a single instance.

10. The apparatus of claim 9, wherein the photon emitter is a first photon emitter, the apparatus further comprising a second photon emitter configured to direct photons into an internal region of the article, wherein the first and second photon emitters emit photons from different locations of the circumferential edge.

11. The apparatus of claim 9 further comprising a stage configured to hold the article and further configured to transmit photons emitted from the photon emitter to the circumferential edge of the article.

12. The apparatus of claim 11, wherein the stage includes a clamp configured to fasten to the edge of the article; and wherein the clamp includes an inlet configured to provide photons emitted from the photon emitter to the edge of the article.

13. The apparatus of claim 9, wherein the camera is selected from the group consisting of a complementary metal-oxide semiconductor ("CMOS") camera and a scientific complementary metal-oxide semiconductor ("sCMOS") camera.

14. The apparatus of claim 10, wherein the first and second photon emitters simultaneously emit photons into the internal region of the article.

15. A method comprising:
emitting photons having a first wavelength from a first photon emitter to an inlet of a clamp, wherein the claim is positioned on an inner circumferential edge of an article to internally reflect the photons within the article;
after emitting the photons having the first wavelength, emitting photons having a second wavelength from a second photon emitter into the article from the edge of the article to internally reflect the photons within the article;
scattering the photons at a feature of the article; and
detecting the scattering with a photon detector array.

16. The method of claim 15 further comprising prior to emitting the photons having the first wavelength, mounting the article on a stage, wherein emitting the photons having the first wavelength includes transmitting the photons via the stage to the edge of the article.

17. The method of claim 16, wherein emitting the photons having the first wavelength includes emitting the photons into the article via an inlet of a clamp of the stage fastened at the edge of the article.

18. The method of claim 15, wherein emitting the photons having the first wavelength includes emitting the photons into the article from the edge at an angle that produces an angle of refraction greater than 90 degrees.

19. The method of claim 15 further comprising after emitting the photons having the second wavelength, emitting photons having a third wavelength from a third photon emitter into the article from the edge of the article to internally reflect the photons within the article.

* * * * *